(12) United States Patent
Heine et al.

(10) Patent No.: US 9,662,309 B2
(45) Date of Patent: May 30, 2017

(54) ANTI-DEMODICOSIS AGENT

(75) Inventors: Josef Heine, Leichlingen (DE); Klemens Krieger, Lindlar (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 31 days.

(21) Appl. No.: 11/718,914

(22) PCT Filed: Oct. 27, 2005

(86) PCT No.: PCT/EP2005/011484
§ 371 (c)(1),
(2), (4) Date: May 9, 2007

(87) PCT Pub. No.: WO2006/050816
PCT Pub. Date: May 18, 2006

(65) Prior Publication Data
US 2008/0039519 A1 Feb. 14, 2008

(30) Foreign Application Priority Data
Nov. 9, 2004 (DE) ........................ 10 2004 053 964

(51) Int. Cl.
*A61K 31/33* (2006.01)
*A61K 31/365* (2006.01)

(52) U.S. Cl.
CPC .................................. *A61K 31/365* (2013.01)

(58) Field of Classification Search
CPC ........ A01N 31/00; A01N 31/02; A01N 31/06; A01N 25/00; A01N 25/02; A01N 25/04; A01N 25/10; A01N 33/00; A01N 33/02; A01N 33/04; A01N 33/06; A01N 33/16; A01N 33/18; A01N 33/26; A61K 31/365
USPC ................................................... 514/30, 450
See application file for complete search history.

(56) References Cited

U.S. PATENT DOCUMENTS

| | | | |
|---|---|---|---|
| 4,199,569 A | 4/1980 | Chabala et al. | |
| 4,310,519 A | 1/1982 | Albers-Schonberg et al. | |
| 4,916,120 A * | 4/1990 | Roben et al. | 514/30 |
| 5,952,372 A | 9/1999 | McDaniel | |
| 6,063,394 A * | 5/2000 | Grosse-Bley et al. | 424/422 |
| 6,426,333 B1 * | 7/2002 | Huet et al. | 514/30 |
| 6,797,701 B2 | 9/2004 | Lukas et al. | |
| 7,514,464 B2 * | 4/2009 | Billen et al. | 514/406 |
| 7,728,011 B2 * | 6/2010 | Sirinyan et al. | 514/341 |
| 2002/0037863 A1 * | 3/2002 | Geary | 514/28 |
| 2003/0050327 A1 * | 3/2003 | Huet et al. | 514/341 |
| 2003/0055089 A1 * | 3/2003 | Sirinyan et al. | 514/341 |
| 2004/0161441 A1 | 8/2004 | Sirinyan et al. | |
| 2004/0198676 A1 * | 10/2004 | Soll et al. | 514/28 |

FOREIGN PATENT DOCUMENTS

| | | |
|---|---|---|
| EP | 0 421 568 A | 4/1991 |
| EP | 0 423 445 A1 | 4/1991 |
| GB | 1 390 336 | 4/1975 |
| WO | 92/08455 A | 5/1992 |

OTHER PUBLICATIONS

Paradis et al. Topical (pour on ) invermectin in the treatment of chronic generalized demodicosis in dogs, Veterinary Medicine 1998, 9, 55-59.*
Paradis et al. New approaches to the treatment of canine demodicosis, Dermatology, vol. 29, No. 6, Nov. 1999.*
Ahmed et al. Pharmaceutical challenges in veterinry product development, Advanced drug delivery reviews, vol. 54, issue 6, Oct. 2002, pp. 871-882.*
Paul et al. (Veterinary Parasitology; vol. 121, pp. 285-291; 2004).*
Galinsky et al. ["Basic Pharmacokinetics and Pharmacodynamics." in: Remington: The Science and Practice of Pharmacy (Baltimore, Lippincott Williams & Wilkins, 2006), p. 1711.].*
Fourie et al. (Parasitol Res, vol. 90, pp. S135-S136; 2003).*
Clark (From STN Search, Jour Econ Ent, vol. 46, No. 6, p. 1093, abstract; 1953).*
Lonneux et al (Veterinary Parasitology, 1992, 45(1-2), 147-152, abstractt).*
Paradis (Dermatology, 1999, 29(6), 1425-1436).*
Database Biosis 'Online! Biosciences Information Service, Philadelphia, PA, US, 2003, Strabel D et al, "Treatment with Avermectins in Two Goats with Demodicosis," Schweizer Archiv Fuer Tierheilkunde, vol. 145, No. 12, 2003, pp. 585-588.
Mueller Ralf S, "Treatment Protocols for Demodicosis: An Evidence-based Review," Veterinary Dermatology, vol. 15, No. 2, Apr. 2004, pp. 75-89.
Heine J et al, "Evaluation of the Efficacy and Safety of Imidacloprid 10% plus Moxidectin 2.5% Spot-on in the Treatment of Generalized Demodicosis in Dogs: Results of a European Field Study," Parasitology Research 2005 Germany, vol. 97, No. Suppl. 1, 2005, pp. S89-S96.
Paradis M, "New Approaches to the Treatment of Canine Demodicosis," The Veterinary Clinics of North America, Small Animal Practice, vol. 29, No. 6, Nov. 1999, pp. 1425-1436.
PCT International Search Report dated Oct. 2, 2006, 8 pgs.
Ide et al., "Milbemycin: Discovery and Development," Annu. Rep. Sankyo Res. Lab. 45 (1993), pp. 1-98.
"Ivermectin and Abamectin," W.C. Campbell, Ed., Springer Verlag, New York, 1989.
"Avermectins and Milbemycins Part II," H.G. Davies et al., Chem. Soc. Rev. 20 (1991) pp. 271-339.
Chemische Modifikationen in: G. Lukacs et al. (Eds.), Springer-Verlag, New York (1990), Chapter 3.
Carter et al., "Structure Determination of LL-F28249alpha, beta, epsilon, and gamma, Potent Antiparasitic Macrolides from *Streptomyces cyaneogriseus* ssp. noncyanogenus," J. Chem. Soc. Chem. Commun. (1987), pp. 402-404.
Goudie et al., "Doramectin—a potent novel endectocide," Vet. Parasitol. 49 (1993), pp. 5-15.
General Chemistry-Principles, Patterns, and Applications, Chapter 4.2 "Solution Concentrations," Saylor.org/Books, pp. 320-321, downloaded Sep. 30, 2014.

(Continued)

*Primary Examiner* — Jason Sims
*Assistant Examiner* — Ibrahim D Bori
(74) *Attorney, Agent, or Firm* — McBee Moore Woodward & Vanik IP, LLC

(57) ABSTRACT

The present invention relates to the use of macrocyclic lactones for treating demodicosis, particularly in dogs.

20 Claims, No Drawings

(56) References Cited

OTHER PUBLICATIONS

Paradis et al., "Topical (pour-on) ivermectin in the treatment of chronic generalized demodicosis in dogs," Veterinary Dermatology, 1998, 9(1): 55-59.

Wagner, R. et al., "Field efficacy of moxidectin in dogs and rabbits naturally infested with *Sarcoptes*, spp., *Demodex* spp. and *Psoroptes* ssp. mites", Veterinary Parasitology 93 (2000) 149-158.

Li, A. Y., et al., "Detection and Characterization of Amitriaz Resistance in the Southern Cattle Tick, Boophilus microplus (Acari: Ixodidae)," Journal of Medical Entomology, 2004, 41(3), pp. 193-200.

Barragry, T. B., "A Review of the Pharmacology and Clinical Uses of Ivermectin," The Canadian Veterinary Journal, 1987, 28(8), pp. 512-517.

Mueller, R. S., et al.,"Treatment of demodicosis in dogs: 2011 clinical practice guidelines," Veterinary Dermatology, 2012, 23, pp. 86-e21.

Muller, H.M., D.V.M., et al., Small Animal Dermatology, Fourth Edition, "Chapter 8. Curaneous Parasitology," 1989, W.B. Saunders Company, Harcourt Brace Jovanovich, Inc., pp. 390-391, 3 pages.

The Merck Veterinary Manual, Ninth Edition, "Mange", 2005, Cynthia M. Kahn, Ed., Merck & Co., Inc., Whitehouse Station, NJ, pp. 743-749, 6 pages.

* cited by examiner

ANTI-DEMODICOSIS AGENT

The present invention relates to the use of macrocyclic lactones for treating demodicosis, particularly in dogs.

In veterinary medicine, macrocyclic lactones are known, in particular, as being agents which exhibit both an outstanding endoparasiticidal effect and, within certain limits, an ectoparasiticidal effect. Thus, these compounds are known, for example, to have an effect against ectoparasitic arthropods.

In the case of demodicosis, particularly in dogs, a distinction is made between a juvenile, as a rule self-healing, local disease (localized demodicosis) and a generalized disease which occurs in the adult animal (generalized demodicosis). Generalized demodicosis is a severe clinical disease which is extremely difficult to treat. While bathing with acaricidal agents, e.g. ronnel (O,O-dimethyl O-(2,4,5-trichlorophenyl)phosphorothioate), was initially used for treating demodicosis, these treatments have to be rejected because of a high risk of the dog and user being poisoned. Bathing with amitraz ((N'-2,4-dimethylphenyl)-N[[(2,4-dimethylphenyl)imino]methyl]methaneimidamide) at intervals of 1-2 weeks constitutes a more modern means of treatment. Success has likewise been achieved using macrocyclic lactones, which are administered orally or by injection at daily to weekly intervals or at 2-weekly intervals. These treatment programmes are expensive for the animal owner and unpleasant for the dog and the owner; success is not assured. Spot-on treatment 3 times weekly with ivermectin has been described in the prior art as being insufficiently effective. The prior art with regard to demodicosis treatment is described in: R. S. Mueller, Veterinary Dermatology, 15 (2004) 75-89; M. Paradis, Veterinary Clinics of North America: Small Animal Practice, 29(6) (1999) 1425-1436.

It has now been found, surprisingly, that a good effect against demodicosis can also be achieved when using macrocyclic lactones externally.

The invention therefore relates to the use of macrocyclic lactones for producing pharmaceuticals to be used externally for treating demodicosis.

Within the meaning of this invention, macrocyclic lactones are, in particular, avermectins, $B_1$ 22,23-dihydroavermectins (ivermectins) or milbemycins.

Avermectins were isolated, as microbial metabolites, from the microorganism *Streptomyces avermitilis* (U.S. Pat. No. 4,310,519) and can essentially occur as a mixture consisting of the eight components $A_{1a}$, $A_{1b}$, $A_{2a}$, $A_{2b}$, $B_{1a}$, $B_{1b}$, $B_{2a}$ and $B_{2b}$, (I. Putter et al. Experentia 37 (1981) p. 963, Birkhäuser Verlag (Switzerland)). In addition, the synthetic derivatives, in particular 22,23-dihydroavermectin $B_1$ (ivermectin), are also of interest (U.S. Pat. No. 4,199,569). It has likewise been possible to isolate milbemycin B-41 D fermentatively from *Streptomyces hygroscopicus* (cf. "Milbemycin: Discovery and Development" I. Junya et al. Annu. Rep. Sankyo Res. Lab. 45 (1993), pp. 1-98; JP Pat. 8 378 549; GB 1 390 336).

It has long been known to use avermectins, $B_1$ 22,23-dihydroavermectins (ivermectins) and milbemycins from the macrocyclic lactone class as endoparasiticides, and this use has been the subject-matter of a large number of patent applications and reviews (e.g. biological effects in "Ivermectin and Abamectin" W. C. Campbell, Ed., Springer Verlag, New York, N.Y., 1989; "Avermectins and Milbemycins Part II" H. G. Davies et al. Chem. Soc. Rev. 20 (1991) pp. 271-339; chemical modifications in: G. Lukacs et al. (Eds.), Springer-Verlag, New York, (1990), Chapter 3; Cydectin™ [moxidectin and derivatives]: G. T. Carter et al. J. Chem. Soc. Chem. Commun. (1987), pp. 402-404); EP 423 445-A1). It is likewise known to use doramectin (Pfizer) as an endoparasiticidal agent (cf. "Doramectin—a potent novel endectocide" A. C. Goudie et al. Vet. Parasitol. 49 (1993), pp. 5-15).

The avermectins are macrolide lactone compounds or compound mixtures of the general formula (I)

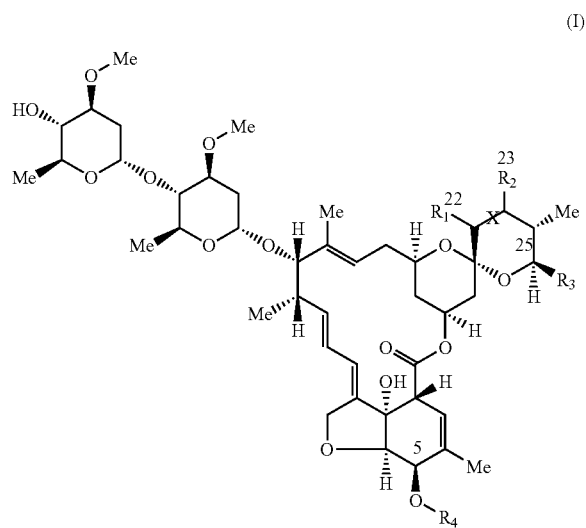

in which the radicals $R^1$ to $R^4$ have the meanings given in Table 1 below and X can be a single or double bond between the $C_{22}$ and $C_{23}$ positions ($—C_{22}R^1—X—C_{23}R^2—$).

When the bond is double, there are no substituents ($R^1$, $R^2$) at the $C_{22}$ and $C_{23}$ positions.

TABLE 1

| Macrocyclic lactone | $—C_{22}R^1—X—C_{23}R^2—$ | $R^3$ | $R^4$ |
| --- | --- | --- | --- |
| avermectin $A_{1a}$ | —CH=CH— | -sec-Bu | -Me |
| avermectin $A_{1b}$ | —CH=CH— | -iso-Pr | -Me |
| avermectin $A_{2a}$ | —CH$_2$—CHOH— | -sec-Bu | -Me |
| avermectin $A_{2b}$ | —CH$_2$—CHOH— | -iso-Pr | -Me |
| avermectin $B_{1a}$ | —CH=CH— | -sec-Bu | —H |
| avermectin $B_{1b}$ | —CH=CH— | -iso-Pr | —H |
| avermectin $B_{2a}$ | —CH$_2$—CHOH— | -sec-Bu | —H |
| avermectin $B_{2b}$ | —CH$_2$—CHOH— | -iso-Pr | —H |
| 22,23-dihydroavermectin $B_{1a}$ | —CH$_2$—CH$_2$— | -sec-Bu | —H |
| 22,23-dihydroavermectin $B_{1b}$ | —CH$_2$—CH$_2$— | -iso-Pr | —H |
| doramectin | —CH=CH— | -Chx | —H |

22,23-dihydroavermectin $B_1$ stands for ivermectin $B_1$;
sec-Bu = secondary butyl; iso-Pr = isopropyl; Chx = cyclohexyl; -Me = methyl As a rule, the avermectins and $B_1$ 22,23-dihydroavermectins (ivermectins) of the general formula (I) are used as mixtures. The product abamectin, which essentially contains the B₁ avermectins, and their hydrogenation products the B₁ 22,23-dihydroavermectins (ivermectin) are of particular interest in this connection.

The macrocyclic lactone compounds which are designated "b", and which have an isopropyl radical in the $C_{25}$ position, do not necessarily have to be separated from the "a" compounds, which have a sec-butyl group in the $C_{25}$ position. A mixture of the two substances consisting of >80% m/m sec-butyl derivative ($B_{1a}$) and <20% m/m isopropyl derivative ($B_{1b}$) is generally isolated and can be used in accordance with the invention. Furthermore, the substituents in the $C_{13}$ and $C_{23}$ positions in the stereoisomers can be arranged either in the α position or in the β position on the ring system, i.e. be located above or below the plane of the molecule. In any case, all the stereoisomers are allowed for in accordance with the invention. In the literature, the 4:1 mixture of avermectin $B_{1a}$ and avermectin $B_{1b}$ is termed abamectin.

Furthermore, the semisynthetic macrocyclic lactone selamectin (5-hydroxyimino-25-cyclohexylavermectin B₁ monosaccharide) is derived from the avermectins:

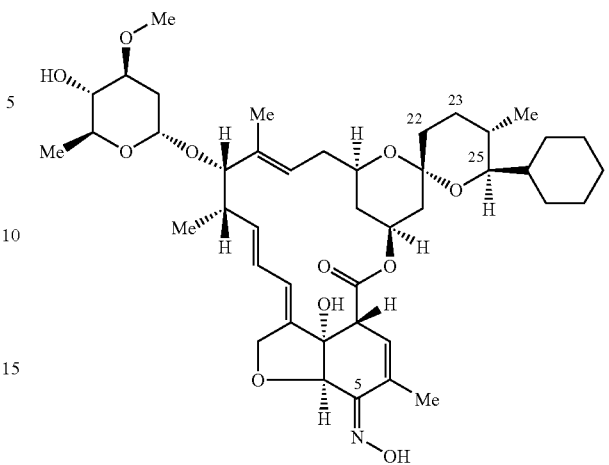

Eprinomectin ((4"R)-4"-(acetylamino)-4"-deoxyavermectin B₁) is likewise derived from the avermectins; this term is understood as meaning a mixture of 90% or more of component $B_{1a}$ and 10% or less of component $B_{1b}$:

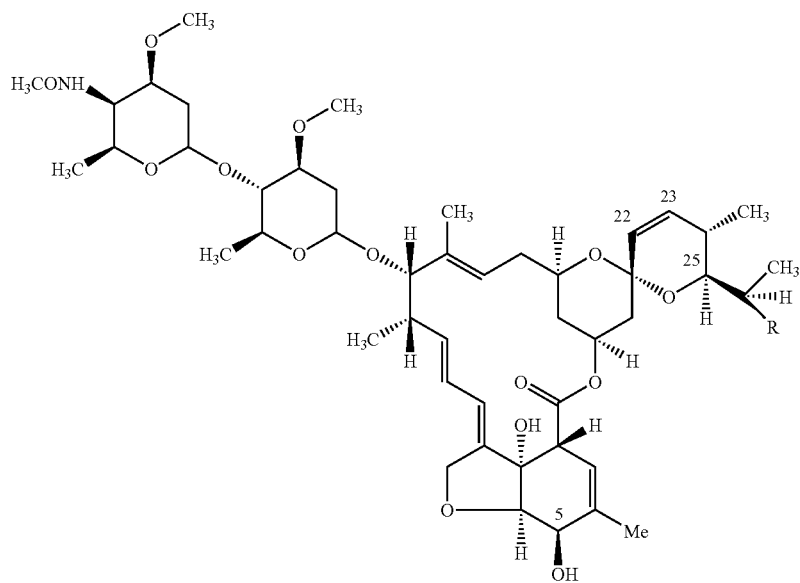

Component $B_{1a}$: R=$C_2H_5$

Component $B_{1b}$: R=$CH_3$

While the milbemycins have the same macrolide ring structure as avermectins or $B_1$ 22,23-dihydroavermectins (ivermectins), they do not carry any substituent (i.e. missing oleandrose disaccharide fragment) at position 13 ($R^5$=hydrogen).

Milbemycins from the class of macrocyclic lactones which may be mentioned by way of example are the compounds having the general formula (II)

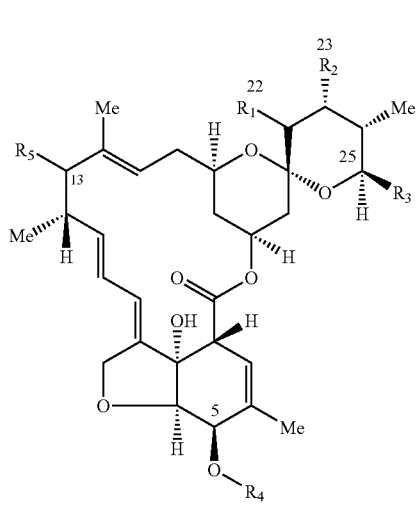

(II)

in which the radicals $R^1$ to $R^5$ have the meanings given in Table 2 below:

TABLE 2

| Macrocyclic lactone | $R^1$ | $R^2$ | $R^3$ | $R^4$ | $R^5$ |
|---|---|---|---|---|---|
| milbemycin B41 D | —H | —H | -iso-Pr | —H | —H |
| nemadectin | —H | —OH | | —H | —H |
| moxidectin | —H | =N—O-Me | | —H | —H | iso-Pr = isopropyl

In connection with the milbemycins, mention may also be made of milbemycin oxime, which is as a rule employed as a mixture of 80% milbemycin $A_4$5-oxime and 20% milbemycin $A_3$5-oxime:

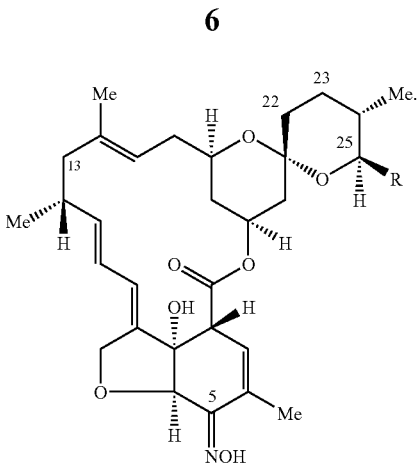

milbemycin $A_4$ oxime: R=—$CH_2CH_3$
milbemycin $A_4$ oxime: R=—$CH_3$

Those of the abovementioned macrocyclic lactones which are of particular interest in accordance with the invention are:

avermectin $B_{1a}/B_{1b}$ (or abamectin)
22,23-dihydroavermectin $B_{1a}/B_{1b}$ (or ivermectin $B_{1a}/B_{1b}$)
doramectin
moxidectin
selamectin
eprinomectin Within the meaning of the invention, the active compounds are also understood as being their pharmaceutically acceptable salts, hydrates and prodrugs, insofar as they can be used.

The abovementioned active compounds can, where appropriate in dependence on the nature and number of the substituents, be present in the form of stereoisomers, e.g. geometric and/or optical isomers, or regioisomers, or in the form of corresponding isomeric mixtures of different composition. Both the pure isomers and the isomeric mixtures having a corresponding effect can be used in accordance with the invention.

Demodicosis is a special form of the disease which is also termed mange ("demodectic mange") and is caused by the hair follicle mites *Demodex* spp., in particular, for example, *Demodex canis*.

While demodicosis can occur in a variety of domestic and productive animals, for example in cattle or cats, it is above all of particular importance in dogs. Preference is therefore given, in accordance with the invention, to treating dogs.

The active compounds can be used either prophylactically or therapeutically.

It has been found that a good and long-lasting effect against demodicosis in the dog can unexpectedly be achieved even when using the macrocyclic lactones externally.

The external use usually takes place in the form of pouring or spotting a small volume, for example of 1-10 ml, onto a part of the body surface of the animal to be treated. In this connection, it was particularly surprising that a good and long-lasting effect can be achieved precisely when externally applying comparatively small volumes; the use according to the invention is therefore simpler and more user-friendly than previously known treatments of demodicosis.

Suitable preparations are:

Solutions, for example solutions for use on the skin or in body cavities, pour-on and spot-on formulations, gels;

Emulsions and suspensions, and semisolid preparations.

Solutions for use on the skin are dripped on, painted on, rubbed in, sprinkled on or sprayed on. These solutions are prepared by dissolving the active compound in a suitable solvent and, if necessary, adding additives such as solubilizers, acids, bases, buffer salts, antioxidants and preservatives; there is no need, in this connection, to operate under sterile conditions.

Solvents which may be mentioned are: physiologically tolerated solvents such as water, alcohols such as ethanol, butanol, benzyl alcohol and glycerol, hydrocarbons, propylene glycol, polyethylene glycols, N-methylpyrrolidone and mixtures thereof.

The active compounds can also, where appropriate, be dissolved in physiologically tolerated vegetable or synthetic oils which are pharmaceutically suitable.

Solubilizers which may be mentioned are: solvents which promote the dissolution of the active compound in the main solvent or prevent its precipitation. Examples are polyvinylpyrrolidone, polyethoxylated castor oil, and polyethoxylated sorbitan esters.

Preservatives are: benzyl alcohol, trichlorobutanol, p-hydroxybenzoic esters and n-butanol.

It may be advantageous to add thickeners during the preparation. Thickeners are: inorganic thickeners, such as bentonites, colloidal silicic acid and aluminium monostearate, and organic thickeners, such as cellulose derivatives, polyvinyl alcohols and their copolymers, acrylates and methacrylates.

Gels are applied to, or painted on, the skin or introduced into body cavities. Gels are prepared by treating solutions, which have been prepared as described above, with sufficient thickener to form a clear mass having an ointment-like consistency. The thickeners which are employed are those mentioned above.

Pour-on formulations are poured or sprinkled onto restricted areas of the skin, with the active compound either penetrating through the skin and acting systemically or being dispersed on the body surface.

Pour-on formulations are produced by dissolving, suspending or emulsifying the active compound in suitable, skin-tolerated solvents or solvent mixtures. Other auxiliary substances such as dyes, absorption-promoting compounds, antioxidants, light-stability agents and adhesives, are added, where appropriate.

Solvents which may be mentioned are: water, alkanols such as ethanol, isopropanol, 2-hexyldecanol, octyldodecanol and tetrahydrofurfuryl alcohol, glycols, such as glycerol, propylene glycol, polyethylene glycols and polypropylene glycols, aromatically substituted alcohols, such as benzyl alcohol, phenylethanol and phenoxyethanol, esters, such as ethyl acetate, butyl acetate, benzyl benzoate, dibutyl adipate, dicaprylyl carbonate, diethylhexyl carbonate and propylene carbonate, ethers, such as dicaprylyl ether, alkylene glycol alkyl ethers, such as dipropylene glycol monomethyl ether and diethylene glycol monoethyl ether, ketones, such as acetone, methyl ethyl ketone and methyl isobutyl ketone, aromatic and/or aliphatic hydrocarbons, vegetable or synthetic fatty oils such as groundnut oil, olive oil, rape-seed oil, sesame oil, soyabean oil and sunflower oil, glyceryl ricinoleate, medium-chain triglycerides, propylene glycol dicaprylate/dicaprate, propylene glycol dipelargonate and propylene glycol laurate; other fatty acid esters such as 2-octyldodecyl myristate, cetearyl isononanoate, cetearyl octanoate, cetyl ethyl hexanoate, cococaprylate/caprate, decyl cocoate, decyl oleate, ethyl oleate, isocetyl palmitate, isopropyl myristate, isopropyl palmitate, isostearyl isostearate, octyl palmitate, octyl stearate and oleyl erucate; silicone oils such as cetyldimethicone, dimethicone and simethicone; dimethylformamide, dimethylacetamide, glycerol formal, glycofurol, 2-pyrrolidone, N-methylpyrrolidone, 2-dimethyl-4-hydroxymethylene-1,3-dioxolane and dioctylcyclohexane.

Dyes are all dyes which are authorized for use in animals and which can be dissolved or suspended.

Examples of absorption-promoting compounds are DMSO, spreading oils such as isopropyl myristate, isopropyl palmitate and dipropylene glycol pelargonate, silicone oils, fatty acid esters, triglycerides and fatty alcohols.

Antioxidants are sulphites or metabisulphites such as potassium metabisulphite, ascorbic acid, butylhydroxytoluene, butylhydroxyanisole and tocopherol.

Examples of light-stability agents are substances from the benzophenone or novantisolic acid class.

Examples of adhesives are cellulose derivatives, starch derivatives, polyacrylates and natural polymers such as alginates and gelatin.

Emulsions are either of the water-in-oil type or of the oil-in-water type.

They are prepared by dissolving the active compound either in the hydrophobic phase or in the hydrophilic phase and homogenizing this phase with the solvent of the other phase using suitable emulsifiers and, where appropriate, other auxiliary substances such as dyes, absorption-promoting compounds, preservatives, antioxidants, light-stability agents and viscosity-increasing compounds.

Hydrophobic phases (oils) which may be mentioned are: paraffin oils, silicone oils, natural vegetable oils such as sesame oil, almond oil and castor oil, synthetic triglycerides such as caprylic/capric acid triglyceride, a triglyceride mixture containing plant fatty acids of $C_{8-12}$ chain length or other specially selected natural fatty acids, partial glyceride mixtures of saturated or unsaturated, where appropriate also hydroxyl group-containing fatty acids, and mono- and diglycerides of the $C_8/C_{10}$ fatty acids.

Fatty acid esters such as ethyl stearate, di-n-butyryl adipate, hexyl laurate and dipropylene glycol pelargonate, esters of a branched fatty acid of medium chain length with saturated fatty alcohols of $C_{16}$-$C_{18}$ chain length, isopropyl myristate, isopropyl palmitate, caprylic/capric esters of saturated fatty alcohols of $C_{12}$-$C_{18}$ chain length, isopropyl stearate, oleyl oleate, decyl oleate, ethyl oleate, ethyl lactate, waxy fatty acid esters such as synthetic duck tail gland fat, dibutyl phthalate, diisopropyl adipate, ester mixtures related to the latter, etc.

Fatty alcohols such as isotridecyl alcohol, 2-octyldodecanol, cetylstearyl alcohol and oleyl alcohol.

Fatty acids such as oleic acid and their mixtures.

Hydrophilic phases which may be mentioned are:

Water, alcohols such as ethanol, isopropanol, propylene glycol, glycerol and sorbitol, and their mixtures.

Emulsifiers which may be mentioned are: nonionic surfactants, for example polyethoxylated castor oil, polyethoxylated sorbitan monooleate, sorbitan monostearate, glycerol monostearate, polyoxyethyl stearate and alkylphenol polyglycol ethers;

ampholytic surfactants such as di-Na-N-lauryl-β-iminodipropionate or lecithin;

anionic surfactants, such as Na lauryl sulphate, fatty alcohol ether sulphates, and mono/dialkyl polyglycol ether ortho-phosphoric acid ester monoethanolamine salt;

cationic surfactants such as cetyltrimethylammonium chloride.

Other auxiliary substances which may be mentioned are: compounds which increase viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers composed of methyl vinyl ether and maleic anhydride, polyethylene glycols, waxes, colloidal silicic acid, or mixtures of the compounds mentioned.

Suspensions are prepared by suspending the active compound in a carrier liquid, where appropriate in the added presence of other auxiliary substances such as wetting agents, dyes, absorption-promoting compounds, preservatives, stabilizers, antioxidants and light-stability agents.

Carrier liquids which may be mentioned are any homogeneous solvents and solvent mixtures.

Wetting agents (dispersing agents) which may be mentioned are the above-specified surfactants.

Other auxiliary substances which may be mentioned are those specified above.

Semisolid preparations only differ from the above-described suspensions and emulsions in having a higher viscosity.

The macrocyclic lactones can also be present in combination with synergists or with other active compounds. Preference is given to the lactones being combined with insecticides from the group comprising agonists of the nicotinergic acetylcholine receptors of insects, specifically and preferably with neonicotinoids. Combinations of this nature can be used to control ectoparasitic insects and endoparasites in addition to demodicosis.

Neonicotinoids are to be understood, in particular, as being compounds of the formula (I):

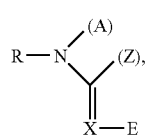

in which
R is hydrogen, or optionally substituted radicals of the group acyl, alkyl, aryl, aralkyl, heteroaryl, heteroarylalkyl or heterocyclylalkyl;
A is a monofunctional group from the series hydrogen, acyl, alkyl or aryl, or is a bifunctional group which is linked to the radical Z;
E is an electron-withdrawing radical;
X is the radicals —CH= or =N—, where the radical —CH= can be linked to the radical Z instead of to an H atom;
Z is a monofunctional group from the series alkyl, —O—R, —S—R and

where
R is identical or different radicals and has the above-mentioned meaning,
or Z is a bifunctional group which is linked to the radical A or to the radical X.

Particular preference is given to compounds of the formula (I) in which the radicals have the following meanings:
R is hydrogen and also optionally substituted radicals from the series acyl, alkyl, aryl, aralkyl, heteroaryl, heteroarylalkyl and heterocyclylalkyl.
Acyl radicals which may be mentioned are formyl, ($C_{1-8}$-alkyl)carbonyl, ($C_{6-10}$-aryl)carbonyl, ($C_{1-8}$-alkyl)sulphonyl, ($C_{6-10}$-aryl)sulphonyl and ($C_{1-8}$-alkyl)($C_{6-10}$-aryl)phosphoryl, which, for their part, can be substituted.
Alkyls which may be mentioned are $C_{1-10}$-alkyl, in particular $C_{1-4}$-alkyl, in detail methyl, ethyl, i-propyl, or sec- or t-butyl, which, for their part, can be substituted.
Aryl is, in particular, $C_{6-10}$-aryl; examples which may be mentioned are phenyl and naphthyl, in particular phenyl.
Aralkyl is, in particular, ($C_{6-10}$-aryl)($C_{1-4}$-alkyl); examples which may be mentioned are phenylmethyl and phenylethyl.
Heteroaryls which may be mentioned are heteroaryl having up to 10 ring atoms and N, O or S, in particular N, as hetero atoms. The following may be mentioned in detail: thienyl, furyl, thiazolyl, imidazolyl, pyridyl and benzothiazolyl.
Heteroarylalkyl is, in particular, heteroaryl($C_{1-4}$-alkyl), where heteroaryl is defined as above. Examples which may be mentioned are heteroarylmethyl and heteroarylethyl having up to 6 ring atoms and N, O or S, in particular N, as hetero atoms.
Heterocyclyl is, in particular, an unsaturated but not aromatic or saturated heterocycle having up to 6 ring atoms and containing up to 3 hetero atoms selected from N, O and S, for example tetrahydrofuryl.
Heterocyclylalkyl is, in particular, heterocyclyl-$C_{1-2}$-alkyl, e.g.: tetrahydro-furanylmethyl and tetrahydro-furanylethyl.

The following substituents may be mentioned by way of example and by way of preference:
Alkyl preferably having 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio preferably having 1 to 4, in particular 1 or 2, carbon atoms, such as methylthio, ethylthio, n- and i-propylthio and n-, i- and t-butylthio; halogenoalkyl preferably having 1 to 4, in particular 1 or 2, carbon atoms, and, preferably, 1 to 5, in particular 1 to 3, halogen atoms, where the halogen atoms are identical or different and, as halogen atoms, are preferably fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino preferably having 1 to 4, in particular 1 or 2, carbon atoms per alkyl group, such as methylamino, methylethylamino, n- and i-propylamino and methyl-n-butylamino; carboxyl; carbalkoxy preferably having 2 to 4, in particular 2 or 3, carbon atoms, such as carbomethoxy and carboethoxy; sulfo (—$SO_3H$); alkylsulphonyl preferably having 1 to 4, in particular 1 or 2, carbon atoms, such as methylsulphonyl and ethylsulphonyl; arylsulphonyl preferably having 6 or 10 aryl carbon atoms, such as phenylsulphonyl, and also heteroarylamino and heteroarylalkylamino, such as chloropyridylamino and chloro-pyridylmethylamino.

A is, particularly preferably, hydrogen and also optionally substituted radicals from the series acyl, alkyl and aryl which preferably have the meanings given in the case of R. A is, furthermore, a bifunctional group. Mention may be made of optionally substituted alkylene having 1-4, in particular 1-2 C atoms, where the above-listed substituents may be mentioned as substituents and where the alkylene groups can be interrupted by hetero atoms from the series N, O and S.

A and Z can, together with the atoms to which they are bonded, form a saturated or unsaturated heterocyclic ring. The heterocyclic ring can contain a further 1 or 2 identical or different hetero atoms and/or hetero groups. The hetero atoms are preferably oxygen, sulphur or nitrogen and the hetero groups are preferably N-alkyl, where the alkyl of the N-alkyl group preferably contains from 1 to 4, in particular 1 or 2, carbon atoms. Alkyls which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethyleneimine, hexahydro-1,3,5-triazine, morpholine and oxadiazine, which compounds can, where appropriate, preferably be substituted by methyl.

E is an electron-withdrawing radical, where mention may be made, in particular, of $NO_2$, CN, halogenoalkylcarbonyl such as halogeno-$C_{1-4}$-alkylcarbonyl having 1 to 9 halogen atoms, in particular $COCF_3$, and also $C_{1-4}$-alkylsulphonyl and halogeno-$C_{1-4}$-alkylsulphonyl having from 1 to 9 halogen atoms, in particular $SO_2CF_3$.

X is —CH= or —N=

Z is optionally substituted radicals alkyl, —OR, —SR or —NRR, where R and the substituents preferably have the abovementioned meanings.

Z can, apart from the abovementioned ring, form, together with the atom to which it is bonded and the radical

a saturated or unsaturated heterocyclic ring in place of X. The heterocyclic ring can contain a further 1 or 2 identical or different hetero atoms and/or hetero groups. The hetero atoms are preferably oxygen, sulphur or nitrogen and the hetero groups are N-alkyl, where the alkyl or N-alkyl group preferably contains from 1 to 4, in particular 1 or 2, carbon atoms. Alkyls which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethyleneimine, morpholine and N-methyl-piperazine.

Compounds which can very particularly preferably be used in accordance with the invention, and which may be mentioned, are compounds of the general formulae (II), (III) and (IV):

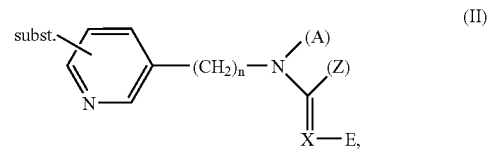

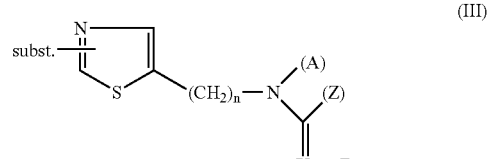

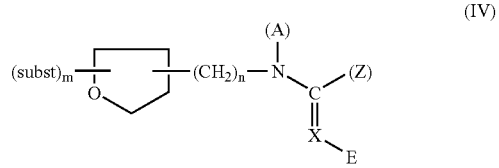

in which n is 1 or 2, m is 0, 1 or 2, subst. is one of the abovementioned substituents, in particular halogen, very particularly chlorine, A, Z, X and E have the abovementioned meanings.

The following compounds may be mentioned individually:
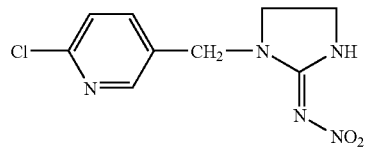
imidacloprid
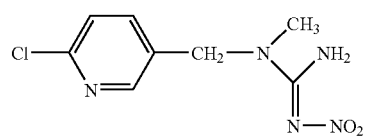
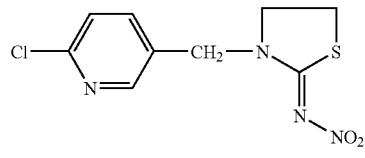
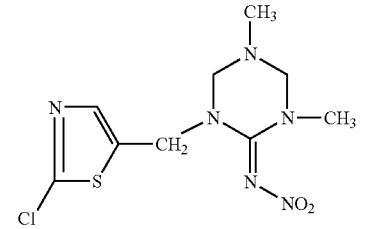
AKD 1022
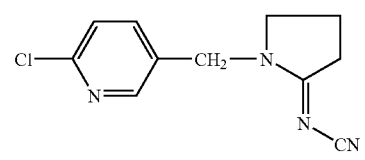
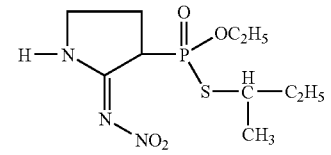
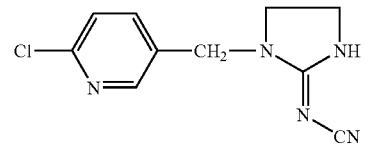
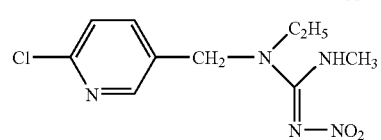
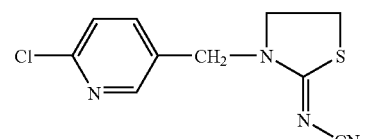
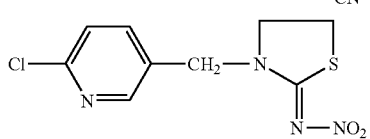
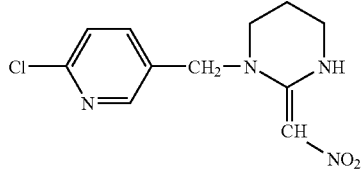
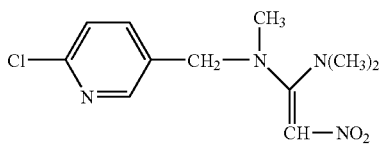
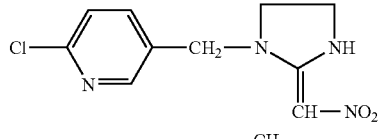
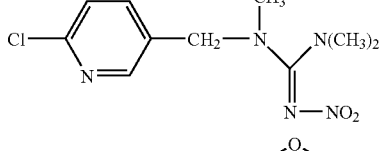
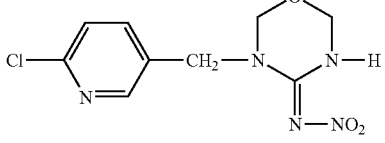
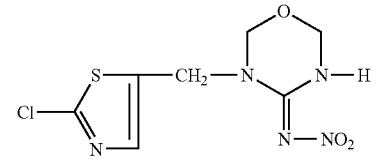
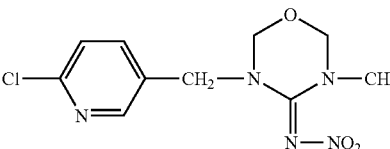
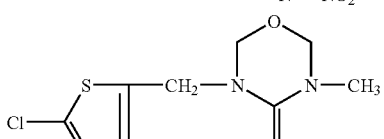
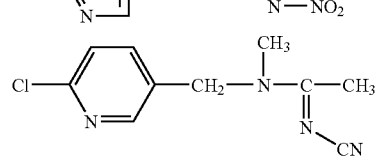
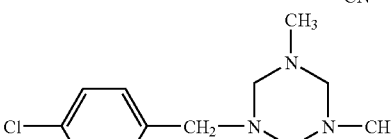
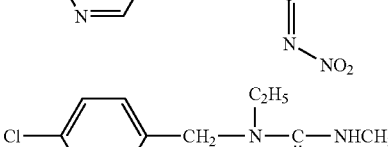

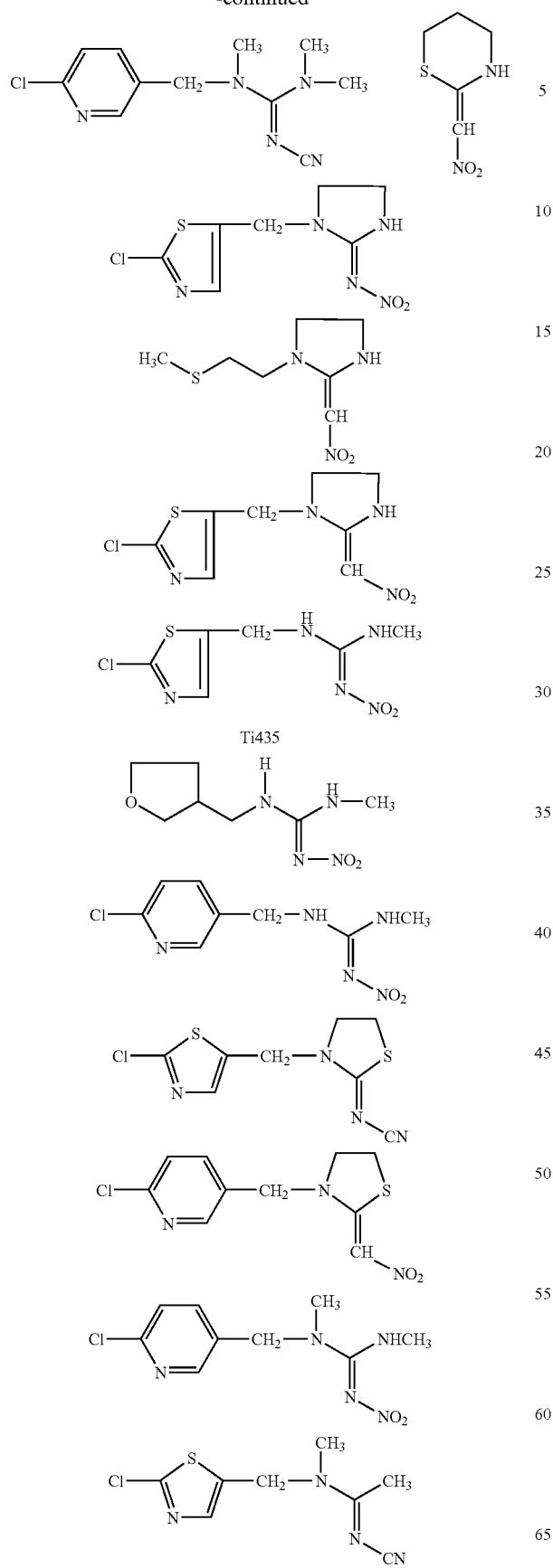
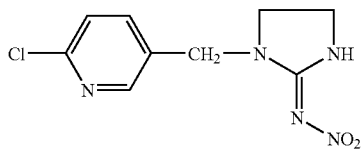
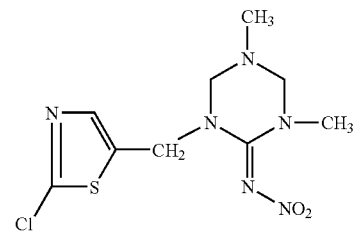
The following particularly preferred compounds may be mentioned individually:
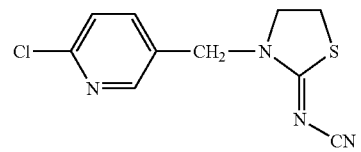
imidacloprid
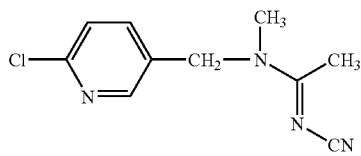
AKD 1022
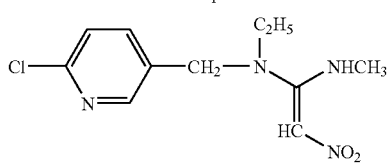
thiacloprid
acetamiprid
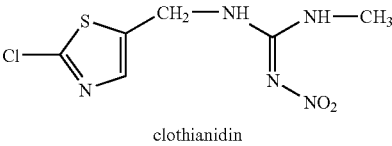
nitenpyram
clothianidin

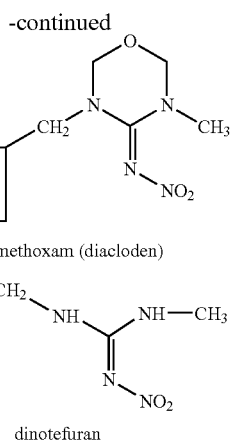

thiamethoxam (diacloden)

dinotefuran

According to the invention, it is also possible to use other nicotinic agonists in addition to nicotinic agonists from the neonicotinoid group.

Ready-to-use preparations of the compositions which can be used in accordance with the invention customarily comprise the active compounds at concentrations of in each case from 10 ppm to 30% m/m; the macrocyclic lactone is preferably employed at concentrations of from 0.01 to 15% m/m, particularly preferably of from 0.02 to 10% m/m; the neonicotinoid is preferably employed at concentrations of from 1 to 20% m/m, particularly preferably of 5-15% m/m.

Preparations which are diluted prior to use comprise the active compounds at correspondingly higher concentrations, for example at from 0.5 to 90% m/m, preferably at from 5 to 50% m/m.

In general, it has proved to be advantageous, for the purpose of achieving effective results, to administer quantities of from about 0.01 to 100 mg of active compound per kg of body weight per day; in the case of the macrocyclic lactone, preferred customary daily doses lie in the range of from 0.05 to 10 mg/kg, particularly preferably of from 0.1 to 8 mg/kg; if a neonicotinoid is employed, customary daily doses preferably lie in the range of from 1 to 20 mg/kg, particularly preferably at 5-10 mg/kg.

According to the invention, particular preference is given to pour-on or spot-on formulations. These are applied, in comparatively small quantities of what is usually from 0.1 to 20 ml, preferably of from 0.4 to 10 ml, to a small part of the body surface of the animal to be treated.

These formulations comprise the macrocyclic lactone in quantities of from 0.01 to 10% m/m, preferably of from 0.02 to 8% m/m.

The content of neonicotinoid, insofar as the latter is employed, is customarily 1-20% m/m, preferably 5-15% m/m.

The solvents which are suitable for the pour-on or spot-on formulations are those which are mentioned above.

In this connection, preference is given to solvents which have very good macrocyclic lactone-dissolving properties, such as ethanol, isopropanol, propylene glycol, 2-hexyldecanol, octyldodecanol, dibutyl adipate, medium-chain triglycerides, propylene glycol dicaprylate/dicaprate, propylene glycol laurate, isopropyl myristate, isopropyl palmitate, propylene carbonate, dipropylene glycol monomethyl ether, diethylene glycol monoethyl ether and ketones.

Preference is also given to solvents which have good spreading properties, such as 2-hexyldecanol, octyldodecanol, 2-octyldodecyl myristate, cetearyl isononanoate, cetearyl octanoate, cetylethyl hexanoate, cococaprylate/caprate, decyl cocoate, decyl oleate, ethyl oleate, isocetyl palmitate, isopropyl myristate, isopropyl palmitate, isostearyl isostearate, octyl palmitate, octyl stearate, oleyl erucate, medium-chain triglycerides, propylene glycol dicaprylate/dicaprate, dipropylene glycol monomethyl ether, diethylene glycol monoethyl ether, cetyldimethicone, dimethicone and simethicone.

In this connection, particular preference is given to solvents which possess good macrocyclic lactone-dissolving properties and possess good spreading properties, such as 2-hexyldecanol, octyldodecanol, dibutyl adipate, dipropylene glycol monomethyl ether, diethylene glycol monoethyl ether, medium-chain triglycerides, propylene glycol-dicaprylate/dicaprate, propylene glycol laurate, isopropyl myristate and isopropyl palmitate.

The solvents can be used alone or in combination. Their total concentration is customarily between 10 and 98% m/m, preferably between 30 and 95% m/m.

In addition to this, the preferred spot-on or pour-on formulations can comprise customary pharmaceutical additives and adjuvants.

Spot-on or pour-on formulations can also be formulated as emulsion concentrates. In this connection, the active compounds are dissolved, at elevated concentration, in a solvent together with a dispersant. The user adds a given quantity of this concentrate to water, whereupon an emulsion forms either spontaneously or after shaking. The above-mentioned substances can be used as solvents while the ionic and nonionic emulsifiers which are likewise mentioned above can be used as dispersants.

If the macrocyclic lactones are used in combination with other active compounds, this means that the macrocyclic lactones and the additional active compound(s) can either be used separately or in a chronologically graduated manner. In this case, the macrocyclic lactones and the active compounds which are additionally employed are in each case formulated as separate pharmaceuticals. Simultaneous use is also possible; according to the invention, preference is given to formulating the macrocyclic lactone and the additional active compound jointly in one composition.

According to a preferred embodiment, use can be made of the formulations which are described in WO 00/30449, which document is hereby expressly incorporated by reference. The formulations which are described in that document are particularly suitable for spot-on application. These formulations comprise:

(a) from 0.1 to 50% w/v, preferably from 1 to 16% w/v, particularly preferably from 4 to 12% w/v, and very particularly preferably from 6 to 12% w/v, of a macrocyclic lactone (b) from 1 to 50% v/v, preferably up to 20% v/v, particularly preferably from 2 to 16% v/v, very particularly preferably from 4 to 12% v/v, in particular from 6 to 12% v/v, of a di($C_{2-4}$-glycol)mono($C_{1-4}$-alkyl)ether (c) an antioxidant, where appropriate, and (d) a skin-tolerated volatile solvent q.s. v/v, where appropriate.

("w/v" means weight/volume; 1% w/v means 1 g in 100 ml of the formulation).

The formulation is suitable for the macrocyclic lactones which are described above in detail, in particular for selamectin.

The di($C_{2-4}$-glycol)mono($C_{1-4}$-alkyl)ether is preferably diethylene glycol monomethyl ether or, in particular, dipropylene glycol monomethyl ether.

The formulation preferably comprises the skin-tolerated volatile solvent; preferred examples are ethanol and, in particular, isopropanol.

Examples of suitable antioxidants are propyl gallate, BHA (2-tert-butyl-4-methoxyphenol) or, in particular, BHT (2,6-ditert-butyl-4-methylphenol). The antioxidant is customarily present in the formulations at concentrations of 0.2% w/v or less, preferably of 0.1% w/v or less.

According to a further particularly preferred embodiment, the following basis is suitable for formulations which can be employed in accordance with the invention, in particular spot-on formulations:

Benzyl alcohol or an optionally substituted pyrrolidone is employed as solvent A. Examples of optionally substituted pyrrolidones are 2-pyrrolidone; 1-($C_1$-$C_{10}$)-2-pyrrolidone, such as 1-methylpyrrolidone, 1-ethylpyrrolidone, 1-octylpyrrolidone, 1-dodecylpyrrolidone, 1-isopropylpyrrolidone, 1-(n-, sec- or tert-butyl)pyrrolidone and 1-hexylpyrrolidone; 1-($C_2$-$C_{10}$-alkenyl)-2-pyrrolidone, such as 1-vinyl-2-pyrrolidone; 1-($C_3$-$C_8$-cycloalkyl)-2-pyrrolidone, such as 1-cyclohexylpyrrolidone; 1-(3-hydroxy-propyl)pyrrolidone, 1-(2-methoxyethyl)pyrrolidone, 1-(3-methoxypropyl)pyrrolidone and 1-benzylpyrrolidone. Of these, particular preference is given to benzyl alcohol.

Preference is given to using the solvent A as a mixture with a cosolvent B which is selected from the cyclic carbonate and lactone group (preferred examples are γ-butyrolactone, ethylene carbonate and, in particular, propylene carbonate) with the proportion of solvent A being from 20 to 99% m/m, preferably from 40 to 90% m/m, particularly preferably from 50 to 90% m/m, and that of solvent B being from 1 to 80% m/m, preferably from 10 to 60% m/m, particularly preferably from 10 to 50% m/m.

The active compound(s), and also, where appropriate, further auxiliary substances and additives, are dissolved in the solvent or solvent mixture.

Formulations of this nature are particularly suitable, for example, for ivermectin or moxidectin, where appropriate in combination with a neonicotinoid such as imidacloprid.

The topical treatment, according to the invention, of demodicosis with macrocyclic lactones makes it possible to treat the disease in a simple and convenient, but nevertheless effective, manner. Applications at intervals of at least one week, preferably of at least two weeks, particularly preferably of at least three weeks and, in particular, every fourth week, are usually sufficient to achieve good treatment results. As a rule, the treatment lasts for from 2 to 4 months.

The following examples of formulations which can be used in accordance with the invention explain the invention without limiting it in any way:

EXAMPLES

Example 1

6% w/v of selamectin
6% v/v of dipropylene glycol monomethyl ether
0.08% w/v of BHT
q.s. 100% v/v of isopropanol Example 2

12% w/v of selamectin
12% v/v of dipropylene glycol monomethyl ether
0.08% w/v of BHT
q.s. 100% v/v of isopropanol Example 3

100 ml of formulation contain:
6.0 g of selamectin
5.63 g of dipropylene glycol monomethyl ether
0.08 g of BHT
69.79 g of isopropanol Example 4

100 ml of formulation contain:
6.0 g of selamectin
5.63 g of dipropylene glycol monomethyl ether
0.08 g of BHT
69.8 g of isopropanol Example 5

10.0 g of imidacloprid
0.08 g of ivermectin
83.1 g of benzyl alcohol
16.5 g of propylene carbonate
0.10 g of BHT Example 6

10.0 g of imidacloprid
0.20 g of ivermectin
83.2 g of benzyl alcohol
16.3 g of propylene carbonate
0.10 g of BHT Example 7

10.0 g of imidacloprid
2.5 g of moxidectin
80.7 g of benzyl alcohol
16.5 g of propylene carbonate
0.10 g of BHT Example 8

10.0 g of imidacloprid
1.0 g of moxidectin
82.2 g of benzyl alcohol 16.5 g of propylene carbonate
0.10 g of BHT Biological Example Field Study: Treating Demodicosis in Dogs A generalized demodicosis in 23 dogs was treated with Advocate® spot-on (100 mg of imidacloprid and 25 mg of moxidectin per ml). The composition was applied in each case once on days 0 and 28; dogs in which it was still possible to detect Demodex mites on day 28 or 56 were treated a third time. Dogs in which it was still possible to detect Demodex mites on day 56 or 84 were treated a fourth time.

87% of the dogs were mite-free at the end of the treatment. Marked improvements in the clinical picture could be observed in the remaining dogs.

The product Interceptor® (tablets containing milbemycin oxime) was tested as a comparison in this study. These tablets were administered orally every day over a period of from 2 to 4 months. While the results with regard to the demodicosis treatment were similar to those obtained with Advocate®, the spot-on application of Advocate® once in 4 weeks is considerably simpler and more convenient than is the daily administration of a tablet as in the case of Interceptor®.

The invention claimed is:

1. A method of treating generalized demodicosis in a dog in need thereof comprising externally applying to the dog a spot-on formulation that comprises a macrocyclic lactone and a combination of solvents A and B, at most once a week, wherein the macrocyclic lactone comprises moxidectin, solvent A is benzyl alcohol or an optionally substituted pyrrolidone and solvent B is a cyclic carbonate or lactone.

2. A method of treating generalized demodicosis in a dog in need thereof comprising externally applying to the dog a spot-on formulation that comprises a mixture of imidacloprid, moxidectin, and a combination of solvents A and B, at most once a week, wherein solvent A is benzyl alcohol or an optionally substituted pyrrolidone, and solvent B is a cyclic carbonate or lactone and wherein the formulation comprises 5 to 15% m/m imidacloprid and 0.02 to 8% m/m moxidectin.

3. The method of claim 1, wherein solvent A is present in an amount of from 50 to 90% m/m and solvent B is present in an amount of from 10 to 50% m/m of the combination of solvents A and B.

4. The method of claim 2, wherein solvent A is present in an amount of from 50 to 90% m/m and solvent B is present in an amount of from 10 to 50% m/m of the combination of solvents A and B.

5. The method of claim 1, wherein solvent A is benzyl alcohol and solvent B is propylene carbonate.

6. The method of claim 2, wherein solvent A is benzyl alcohol and solvent B is propylene carbonate.

7. The method of claim 1, wherein the spot-on formulation has a moxidectin concentration of from 0.1 to 10% m/m.

8. The method of claim 7, wherein the spot-on formulation has a moxidectin concentration of from 0.2 to 8% m/m.

9. The method of claim 1, wherein the spot-on formulation has a total volume of from 0.4 to 10 ml per dose.

10. The method of claim 2, wherein the spot-on formulation has a total volume of from 0.4 to 10 ml per dose.

11. The method of claim 1, wherein the spot-on formulation is applied to the dog at most once every four weeks for 2 to 4 months.

12. The method of claim 2, wherein the spot-on formulation is applied to the dog at most once every four weeks for 2 to 4 months.

13. A method of treating generalized demodicosis in a dog in need thereof comprising externally applying to the dog a spot-on formulation comprising moxidectin, at most once a week.

14. The method of claim 13, wherein the spot-on formulation has a moxidectin concentration of from 0.1 to 10% m/m.

15. The method of claim 14, wherein the spot-on formulation has a moxidectin concentration of from 0.2 to 8% m/m.

16. The method of claim 13, wherein the spot-on formulation has a total volume of from 0.4 to 10 ml per dose.

17. The method of claim 13, wherein the spot-on formulation is applied to the dog at most once every four weeks for 2 to 4 months.

18. The method of claim 13, wherein the spot-on formulation is further comprises imidacloprid.

19. The method of claim 18, wherein the spot-on formulation comprises 5 to 15% m/m imidacloprid and 0.02 to 8% m/m moxidectin.

20. The method of claim 19, wherein the spot-on formulation is applied to the dog at most once every four weeks for 2 to 4 months.

* * * * *